United States Patent
Santilli

(10) Patent No.: US 9,486,195 B2
(45) Date of Patent: *Nov. 8, 2016

(54) SURGICAL RETRACTOR HAVING LIFTING CAPABILITY

(76) Inventor: Albert N. Santilli, Pepper Pike, OH (US)

( * ) Notice: Subject to any disclaimer, the term of this patent is extended or adjusted under 35 U.S.C. 154(b) by 2934 days.

This patent is subject to a terminal disclaimer.

(21) Appl. No.: 11/741,413

(22) Filed: Apr. 27, 2007

(65) Prior Publication Data

US 2007/0203400 A1 Aug. 30, 2007

Related U.S. Application Data

(63) Continuation of application No. 11/162,250, filed on Sep. 2, 2005, now Pat. No. 7,270,632.

(60) Provisional application No. 60/607,474, filed on Sep. 3, 2004.

(51) Int. Cl.
  *A61B 17/02* (2006.01)

(52) U.S. Cl.
  CPC ........... *A61B 17/02* (2013.01); *A61B 17/0293* (2013.01); *A61B 17/0206* (2013.01); *A61B 17/0281* (2013.01)

(58) Field of Classification Search
  CPC .............. A61B 17/02; A61B 17/0293; A61B 17/0281; A61B 17/0206
  USPC .................................................. 600/226–234
  See application file for complete search history.

(56) References Cited

U.S. PATENT DOCUMENTS

| | | | | |
|---|---|---|---|---|
| 432,614 | A | * | 7/1890 | Hendrick ....................... 600/247 |
| 2,920,665 | A | | 1/1960 | Hutson |
| 2,973,792 | A | | 3/1961 | Fonken |
| 3,107,910 | A | | 10/1963 | Wiemken |
| 3,710,783 | A | * | 1/1973 | Jascalevich .................... 600/228 |
| 4,099,521 | A | * | 7/1978 | Nestor et al. .................. 600/228 |
| 4,254,763 | A | * | 3/1981 | McCready et al. ............ 600/230 |
| 4,421,108 | A | * | 12/1983 | Cabrera et al. ................ 600/234 |
| 4,461,284 | A | * | 7/1984 | Fackler .......................... 600/228 |
| 5,000,163 | A | | 3/1991 | Ray et al. |
| 5,088,472 | A | | 2/1992 | Fakhrai |
| RE34,150 | E | | 12/1992 | Santilli et al. |
| 5,365,921 | A | * | 11/1994 | Bookwalter et al. .......... 600/232 |
| 5,520,610 | A | | 5/1996 | Giglio et al. |
| 5,788,630 | A | * | 8/1998 | Furnish ........................... 600/232 |
| 5,795,291 | A | | 8/1998 | Koros et al. |
| 5,879,291 | A | | 3/1999 | Kolata et al. |

(Continued)

*Primary Examiner* — Mary Hoffman
(74) *Attorney, Agent, or Firm* — Wayne D. Porter, Jr.

(57) ABSTRACT

A surgical retractor includes a pair of small grips that are disposed at the ends of arms that can be moved toward or away from each other. The grips engage and separate the sides of an incision that has been made in a patient. A lifting mechanism that can be attached to one of the arms enables one side of the incision to be raised relative to the other side of the incision. The lifting mechanism includes a clamp that can be connected to the retractor and a foot that is connected to the clamp and which is movable relative thereto. The foot is engageable with the patient such that extension of the foot causes a selected grip to be raised. Retraction of the foot permits the selected grip to be lowered. In the preferred embodiment, the foot is disposed at one end of a notched rack; a rotatable pinion is in contact with the notches to extend and contract the rack; and a pivotally movable pawl permits movement of the rack in one direction and prevents movement of the rack in the other direction.

13 Claims, 2 Drawing Sheets

(56) References Cited

U.S. PATENT DOCUMENTS

| | | |
|---|---|---|
| 5,897,490 A | 4/1999 | Fox et al. |
| 5,902,233 A | 5/1999 | Farley et al. |
| 5,908,382 A | 6/1999 | Koros et al. |
| 5,967,974 A | 10/1999 | Nicholas et al. |
| 6,030,340 A | 2/2000 | Maffei et al. |
| 6,099,468 A | 8/2000 | Santilli et al. |
| 6,113,535 A | 9/2000 | Fox et al. |
| 6,241,659 B1 | 6/2001 | Bookwalter et al. |
| 6,361,492 B1 | 3/2002 | Santilli |
| 6,602,190 B2 | 8/2003 | Dobrovolny |
| 6,648,818 B2 | 11/2003 | Cartier et al. |
| 6,712,795 B1 * | 3/2004 | Cohen .......................... 604/233 |
| 6,761,511 B2 | 7/2004 | Turner |
| 7,338,442 B2 * | 3/2008 | Mulac et al. ................. 600/226 |
| 7,654,954 B1 * | 2/2010 | Phillips et al. ............... 600/228 |
| 2002/0026101 A1 | 2/2002 | Bookwalter et al. |
| 2002/0177753 A1 | 11/2002 | Dobrovolny |
| 2003/0021645 A1 | 1/2003 | Turner |
| 2004/0199055 A1 | 10/2004 | Mulac |

* cited by examiner

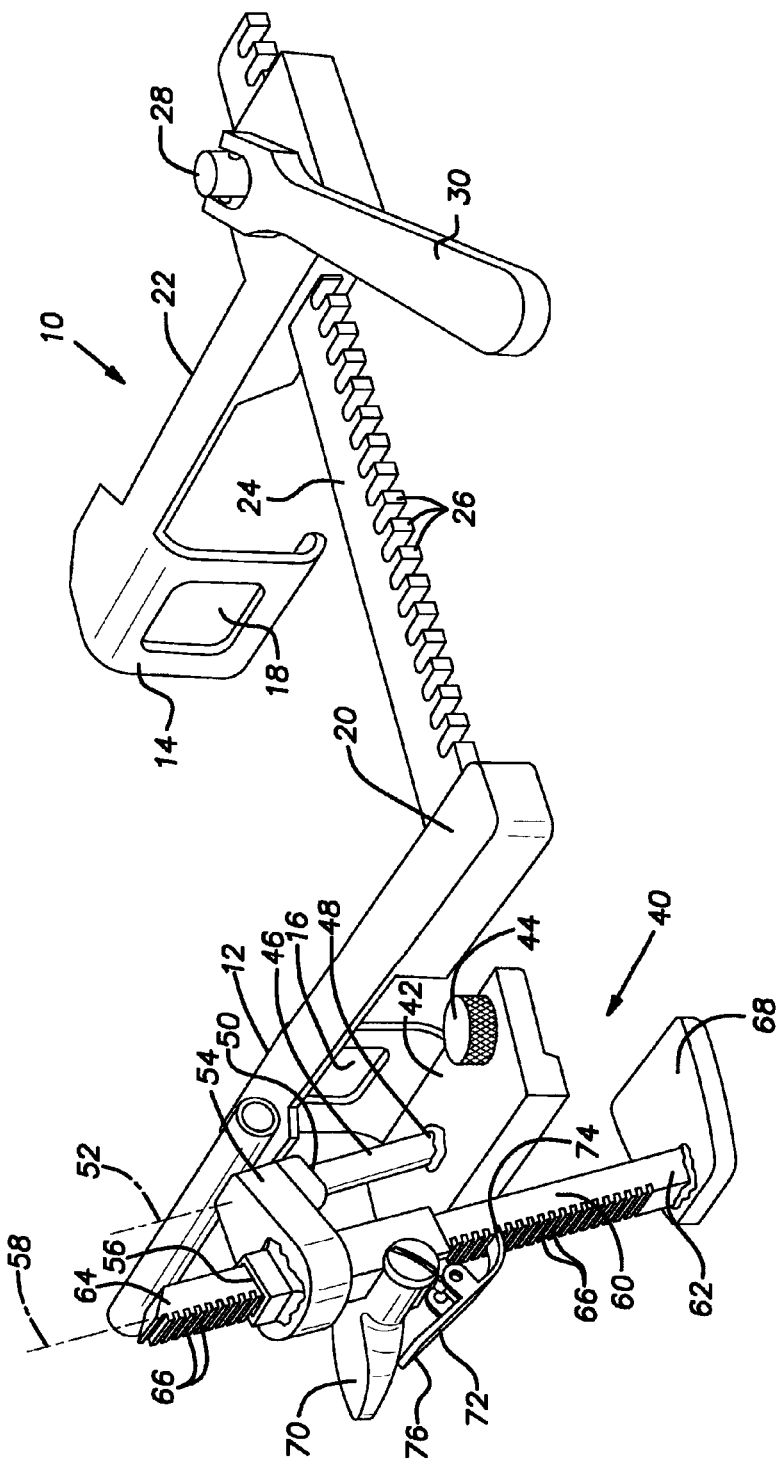

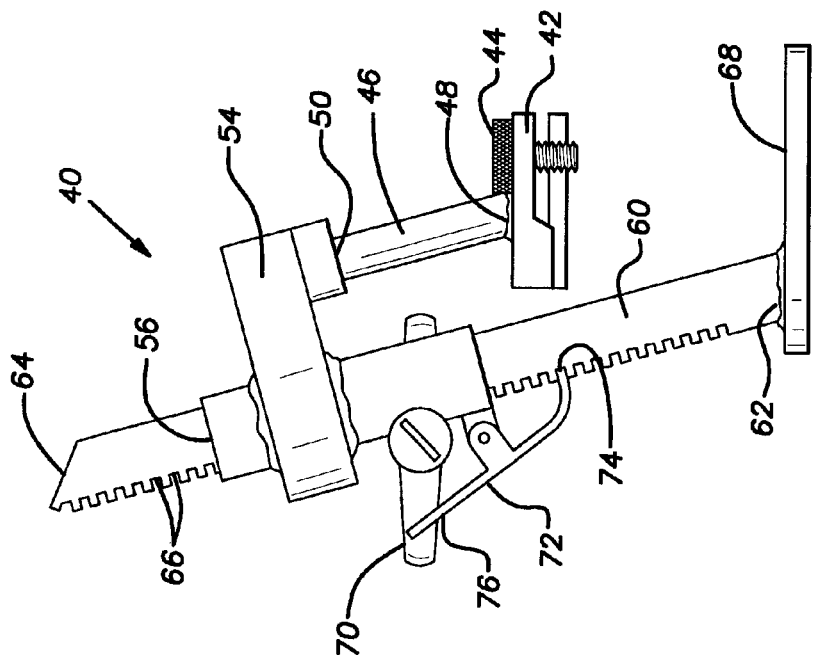
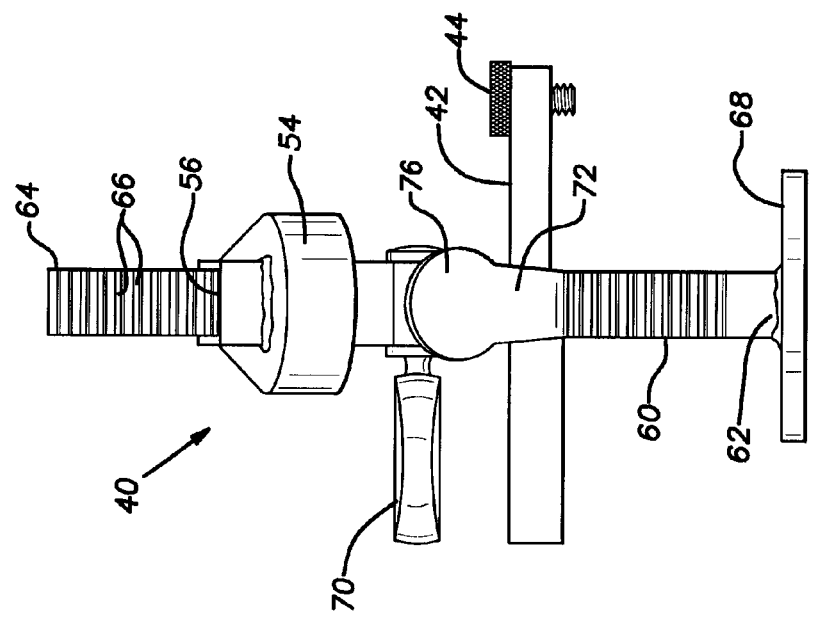

SURGICAL RETRACTOR HAVING LIFTING CAPABILITY

REFERENCE TO RELATED APPLICATION

The present application is a continuation of application Ser. No. 11/162,250, filed Sep. 2, 2005 by Albert N. Santilli, entitled Surgical Retractor Having Lifting Capability, which is now U.S. Pat. No. 7,270,632, which claimed priority from provisional application Ser. No. 60/607,474, filed Sep. 3, 2004 by Albert N. Santilli, entitled Surgical Retractor Having Lifting Capability. The present application claims benefit of the referenced applications and incorporates both of them herein by reference.

BACKGROUND OF THE INVENTION

1. Field of the Invention

The invention relates to retractors that are used in various types of surgeries such as cardiovascular surgery and, more particularly, to a retractor that permits such operations to be conducted with minimal trauma to the patient.

2. Description of the Prior Art

In the course of such operative procedures as mitral valve surgery and mammary artery surgery, it is necessary to expose the heart. Such exposure traditionally has been accomplished by performing a full sternotomy (cutting an incision completely through the sternum and retracting the sternum). The retraction is accomplished by a retractor that employs parallel grips that engage the edges of the separated sternum. The grips are mounted perpendicularly to a toothed crossbar. One of the grips is fixed to one end of the crossbar, while the other grip is movably mounted to the crossbar by means of a pinion that engages the teeth of the crossbar. Upon rotating the pinion, the movable grip can be moved away from the fixed grip, thereby retracting the sternum so as to expose the heart. A retractor of the type described is shown in U.S. Re. 34,150, issued Dec. 29, 1992 to A. E. Santilli and D. M. Cosgrove III ("the '150 patent"), the disclosure of which is incorporated herein by reference.

A surgical retractor that is less invasive than that disclosed in the '150 patent is disclosed in U.S. Pat. No. 6,099,468, issued Aug. 8, 2000 to A. N. Santilli and A. Patel ("the '468 patent"), the disclosure of which is incorporated herein by reference. The retractor according to the '468 patent includes a pair of very small parallel grips that are mounted to a toothed crossbar. As in the device disclosed in the '150 patent, the grips are disposed at the ends of arms that extend at right angles from the crossbar. One of the arms is fixed to one end of the crossbar, while the other arm is movable along the crossbar by means of a pinion so that the grips can be moved toward or away from each other.

The retractor according to the '468 patent is smaller than prior retractors, and therefore less invasive. By using the retractor according to the '468 patent, a partial sternotomy, rather than a full sternotomy, can be performed in order to have access to the heart. While the retractor according to the '468 patent is less invasive, it can retract the sternum or ribs only in one plane. That is, the sternum or ribs are pulled straight apart. There are a variety of circumstances in which it is desirable not only to retract the sternum or ribs, but also to lift one side of the incision relative to the other.

A surgical retractor that permits one side of the incision to be lifted relative to the other side is disclosed in U.S. Pat. No. 6,361,492, issued Mar. 26, 2002 to Albert N. Santilli ("the '492 patent"), the disclosure of which is incorporated herein by reference. As in the device disclosed in the '468 patent, the retractor disclosed in the '492 patent includes relatively small grips or paddles that are inserted through a small opening formed between adjacent ribs or a portion of the sternum. The retractor in question includes a two-part toothed crossbar that has a pivoted connection at or near its center. The retractor has a crank mechanism connected between the opposed arms that permits the arms to be pulled toward or away from each other in order to pivot the crossbar about the pivot. Such pivoting of the crossbar enables one arm to be lifted relative to the other. In turn, one side of the incision can be lifted relative to the other side.

While the device according to the '492 patent is effective to lift one side of the incision, there are many situations in which there is no need, or it is undesired, for the retractor to have pivoting portions. It would be desirable to be able to lift one side of the incision relative to the other without the complexity, expense, or bulkiness of a pivot and accompanying crank mechanism. Any such retractor preferably would permit minimally invasive surgical procedures to be performed.

SUMMARY OF THE INVENTION

In response to the foregoing concerns, the present invention provides a new and improved surgical retractor and lift mechanism therefor. In the preferred embodiment, the retractor according to the invention includes a pair of small grips that are disposed at the ends of arms that are joined by a crossbar. One of the arms is fixed to the crossbar and the other arm can be moved toward or away from the other arm. The arms and the crossbar each include at least one generally flat portion. The grips engage and separate the sides of an incision that has been made in a patient. A lifting mechanism that can be attached to one of the arms or the crossbar enables one side of the incision to be raised relative to the other side of the incision.

The lifting mechanism includes a clamp that can be connected to the retractor and a locking mechanism that selectively locks the clamp to the retractor. The lifting mechanism includes a foot that is connected to the clamp and which is movable relative thereto. The foot is engageable with the patient such that extension of the foot causes the retractor to be raised and contraction of the foot causes the retractor to be lowered.

In the preferred embodiment, the lifting mechanism includes a post having first and second ends and a longitudinal axis, the first end being connected to and extending from the clamp. A formation is connected to the second end of the post, the formation having an opening therethrough, the opening having an axis that is spaced from and generally parallel with the longitudinal axis of the post. A rack having first and second ends and notches along one side is disposed within the opening for movement back and forth therein. The foot is connected to the first end of the rack. A rotatable pinion is carried by the formation, the pinion being in contact with the notches. A wingnut is connected to the pinion, the wingnut being accessible to a user. A pawl having first and second ends is connected to the formation, the first end being biased into contact with the notches and the second end being accessible to a user. The pawl is pivotally mounted to the formation such that the first end permits movement of the rack in one direction and prevents movement of the rack in the other direction.

The lifting mechanism according to the invention is quite compact. It can be attached to the retractor quickly and easily and can be sterilized for indefinite reuse. The foot is designed to press against the patient with relatively low pressure. The interaction of the notches and pawl enables the retractor and, hence, one side of the incision, to be raised in small, carefully controlled increments. When the surgical procedure has been completed and it is desired to remove the retractor, the raised side of the incision can be lowered readily merely by releasing the pawl.

The foregoing and other features and advantages of the invention will be apparent from a review of the following description of the invention, together with the attached drawings.

BRIEF DESCRIPTION OF THE DRAWINGS

FIG. 1 is a perspective view of a lifting mechanism according to the invention disposed in position to be attached to a surgical retractor;

FIG. 2 is a rear view of the lifting mechanism of FIG. 1; and

FIG. 3 is a side elevation view of the lifting mechanism of FIG. 1.

DESCRIPTION OF THE PREFERRED EMBODIMENT

Referring generally to FIGS. 1-3, a surgical retractor according to the invention is indicated generally by the reference numeral 10. The retractor 10 is of the Finochietto type. The retractor 10 includes a pair of small, generally rectangular parallel grips 12, 14. The grips 12, 14 have rectangular openings 16, 18 formed therein, respectively. The grips 12, 14 are mounted at the ends of arms 20, 22, respectively.

The arms 20, 22 extend at right angles away from a crossbar 24 having a plurality of spaced teeth 26. The arm 20 is fixed to the crossbar 24, while the arm 22 is movable along the crossbar 24 so as to move the grip 14 toward or away from the grip 12. Movement of the arm 22 is accomplished by a pinion 28 that engages the teeth 26 of the crossbar 24. A handle 30 is connected to the pinion 28 for purposes of rotating the pinion 28. The arms 20, 22 and the crossbar 24 each define one or more generally flat portions.

Retractor blades and/or stabilizers (not shown) can be attached to the arms 20, 22 in order to retract or stabilize portions of the patient's anatomy. Reference is made to the '150 patent, the '468 patent, and the '492 patent for teachings of representative retractor blades and stabilizers that can be attached to the arms 20, 22.

A lifting mechanism according to the invention is indicated generally by the reference numeral 40. The lifting mechanism 40 includes a locking mechanism in the form of a C-shaped clamp 42 that can be connected to the retractor 10 by being fitted about a selected generally flat portion of one of the arms 20, 22 or the crossbar 24. The clamp 42 includes a pair of spaced-apart members that are generally parallel with each other, the spaced-apart members defining a space therebetween into which a selected generally flat portion can be disposed. The spaced-apart members are joined by a connection along one edge thereof. In the illustrated embodiment, the clamp 42 is connected to the fixed arm 20. The clamp 42 has a threaded opening (not shown) through which a threaded pin 44 extends for engagement with the arm 20.

The lifting mechanism 40 includes a post 46 having first and second ends 48, 50 and a longitudinal axis 52. The first end 48 is connected to and extends from the clamp 42. A formation 54 is connected to the second end 50. The formation 54 has a non-round, preferably square, opening 56 therethrough. The opening 56 has an axis 58 that is spaced from and generally parallel with the longitudinal axis 52 of the post 46.

A rack 60 having first and second ends 62, 64 and notches 66 along one side is disposed within the opening 56 for movement back and forth therein. The cross-section of the rack 60 is of a size and shape to fit snugly in the opening 56. A foot 68 is connected to the first end 62 of the rack 60. The foot 68 is illustrated as being generally rectangular, although it can be of any shape, such as circular, that will exert relatively low pressure on the patient during use. A rotatable pinion (not shown) is carried by the formation 54. The pinion is in contact with the notches 66. A wingnut 70 is connected to the pinion. The wingnut 70 is accessible to the surgeon so that the pinion can be turned readily.

A pawl 72 having first and second ends 74, 76 is pivotally connected to the formation 54. The first end 74 is biased into contact with the notches 66 by means of a spring (not shown) disposed between the second end 76 and the formation 54. The second end is accessible to the surgeon. The pawl 72 is mounted to the formation 54 such that the first end 74 permits movement of the rack 60 in one direction (extension of the foot 68) and prevents movement of the rack 60 in the other direction (contraction of the foot 68) unless the second end 76 has been pressed.

It is expected that the retractor 10 will be used as follows. Initially, the handle 30 will be rotated so that the arm 22 will be moved toward the arm 20. Accordingly, the grips 12, 14 will be immediately adjacent each other. Due to the small size and shape of the grips 12, 14, the thoracic cavity need be opened only a small amount, for example, a distance of about 4 inches. After inserting the grips 12, 14 into the incision, the sternum can be retracted by turning the handle 30 to move the grip 14 away from the grip 12.

Either before or after the grips 12, 14 have been moved apart, the clamp 42 is attached to the arm 20 or the arm 22 or the crossbar 24 and retained there by the threaded pin 44. Thereafter, the wingnut 70 is turned so that the pinion moves the rack 60 in a direction to extend the foot 68. Eventually, the foot 68 will contact the patient. Continued rotation of the wingnut 70 will cause the retractor 10 to be lifted. As a consequence, one side of the incision will be lifted relative to the other side. The wingnut 70 can be rotated in small, carefully controlled increments determined by the spacing of the notches 66. After the desired amount of lifting has been attained, the position of the rack 60 will be maintained by the pawl 72.

After the surgical procedure has been completed, the surgeon can press on the second end 76 of the pawl 72. The first end 74 will be disengaged from the notches 66, thereby permitting the rack 60 to be moved to a contracted position. Thereafter, the retractor 10 can be removed from the patient by reversing the previously described steps.

Although the invention has been described in its preferred form with a certain degree of particularity, it will be understood that the present disclosure of the preferred embodiment has been made only by way of example and that various changes may be resorted to without departing from the true spirit and scope of the invention as hereinafter claimed. It is intended that the patent shall cover, by suitable expression in the appended claims, whatever features of patentable novelty exist in the invention disclosed.

What is claimed is:

1. A lifting mechanism for use with a surgical retractor in a surgical procedure on a patient, the retractor having one or more generally flat portions, comprising:

a clamp that can be connected to the retractor, the clamp being of a size and shape to be disposed about any selected generally flat portion of the retractor;

a locking mechanism to selectively lock the clamp to the selected generally flat portion of the retractor;

a foot connected to the clamp, the foot being movable relative to the clamp while the clamp is connected to the retractor, the foot being engageable with the patient such that extension of the foot causes the retractor to be raised and contraction of the foot causes the retractor to be lowered, whereby the retractor moves along a path;

a post having first and second ends and a longitudinal axis, the first end connected to and extending from the clamp, the longitudinal axis extending generally parallel with the path the retractor moves along when it is raised and lowered;

a formation connected to the second end of the post, the formation having an opening therethrough, the opening having an axis that is spaced from and generally parallel with the longitudinal axis of the post;

a rack having first and second ends and notches along one side, the rack being disposed within the opening for movement back and forth therein, the foot being connected to the first end of the rack;

a rotatable pinion carried by the formation, the pinion being in contact with the notches;

a wingnut connected to the pinion, the wingnut being accessible to a user; and a pawl having first and second ends connected to the formation, the first end being spring-biased toward contact with the notches and the second end being accessible to a user, the pawl being pivotally mounted to the formation such that the first end permits movement of the rack in one direction and prevents movement of the rack in the other direction.

2. The lifting mechanism of claim 1, wherein the opening in the formation is non-round in cross-section and the rack is of a size and shape to fit snugly within the opening.

3. A lifting mechanism for use with a surgical retractor in a surgical procedure, the retractor having first and second arms connected by a crossbar, the first arm being fixed to the crossbar and the second arm being movable along the crossbar toward and away from the first arm, the first and second arms and the crossbar having one or more generally flat portions and each of the first and second arms having grips that engage and separate the sides of an incision that has been made in a patient, the lifting mechanism permitting one side of the incision to be raised relative to the other side of the incision, the lifting mechanism comprising:

a clamp that can be connected to the retractor at any selected generally flat portion;

a locking mechanism to selectively lock the clamp to the selected generally flat portion of the retractor;

a foot connected to the clamp, the foot being movable relative to the clamp while the clamp is connected to the retractor, the foot being engageable with the patient such that extension of the foot causes the retractor to be raised and contraction of the foot causes the retractor to be lowered, whereby the retractor moves along a path;

a post having first and second ends and a longitudinal axis, the first end connected to and extending from the clamp, the longitudinal axis extending generally parallel with the path the retractor moves along when it is raised and lowered;

a formation connected to the second end of the post, the formation having an opening therethrough, the opening having an axis that is spaced from and generally parallel with the longitudinal axis of the post;

a rack having first and second ends and notches along one side, the rack being disposed within the opening for movement back and forth therein, the foot being connected to the first end of the rack;

a rotatable pinion carried by the formation, the pinion being in contact with the notches;

a wingnut connected to the pinion, the wingnut being accessible to a user; and a pawl having first and second ends connected to the formation, the first end being spring-biased toward contact with the notches and the second end being accessible to a user, the pawl being pivotally mounted to the formation such that the first end permits movement of the rack in one direction and prevents movement of the rack in the other direction.

4. The lifting mechanism of claim 3, wherein the opening in the formation is non-round in cross-section and the rack is of a size and shape to fit snugly within the opening.

5. Apparatus for use in a surgical procedure, comprising:

a surgical retractor, the retractor including:

first and second arms connected by a crossbar, the first arm being fixed to the crossbar and the second arm being movable along the crossbar toward and away from the first arm;

grips included as part of the first and second arms that engage and separate the sides of an incision that has been made in a patient; and generally flat portions included as part of the first and second arms and the crossbar; and a lifting mechanism, the lifting mechanism including:

a clamp that can be connected to the retractor at any selected generally flat portion;

a locking mechanism to selectively lock the clamp to the selected generally flat portion of the retractor;

a foot connected to the clamp, the foot being movable relative to the clamp while the clamp is connected to the retractor, the foot being engageable with the patient such that extension of the foot causes the retractor to be raised and contraction of the foot causes the retractor to be lowered, whereby the retractor moves along a path;

a post having first and second ends and a longitudinal axis, the first end connected to and extending from the clamp, the longitudinal axis extending generally parallel with the path the retractor moves along when it is raised and lowered;

a formation connected to the second end of the post, the formation having an opening therethrough, the opening having an axis that is spaced from and generally parallel with the longitudinal axis of the post;

a rack having first and second ends and notches along one side, the rack being disposed within the opening for movement back and forth therein, the foot being connected to the first end of the rack;

a rotatable pinion carried by the formation, the pinion being in contact with the notches;

a wingnut connected to the pinion, the wingnut being accessible to a user; and a pawl having first and second ends connected to the formation, the first end being spring-biased toward contact with the notches and the second end being accessible to a user, the pawl being pivotally mounted to the formation such that the first end permits movement of the rack in one direction and prevents movement of the rack in the other direction.

6. The apparatus of claim 5, wherein the opening in the formation is non-round in cross-section and the rack is of a size and shape to fit snugly within the opening.

7. The lifting mechanism of claim 1, wherein the clamp is generally C-shaped and includes:
   a pair of spaced-apart members that are generally parallel with each other, the spaced-apart members defining a space therebetween into which a selected generally flat portion of the retractor can be disposed; and
   a connection between the spaced-apart members along one edge thereof.

8. The lifting mechanism of claim 1, wherein the locking mechanism comprises:
   a threaded opening in the clamp; and
   a threaded pin that extends through the threaded opening in the clamp, the threaded pin adapted to engage the selected generally flat portion of the retractor.

9. The lifting mechanism of claim 3, wherein the clamp is generally C-shaped and includes:
   a pair of spaced-apart members that are generally parallel with each other, the spaced-apart members defining a space therebetween into which a selected generally flat portion of the retractor can be disposed; and
   a connection between the spaced-apart members along one edge thereof.

10. The lifting mechanism of claim 3, wherein the locking mechanism comprises:
    a threaded opening in the clamp; and
    a threaded pin that extends through the threaded opening in the clamp, the threaded pin adapted to engage the selected generally flat portion of the retractor.

11. The apparatus of claim 5, wherein the clamp is generally C-shaped and includes:
    a pair of spaced-apart members that are generally parallel with each other, the spaced-apart members defining a space therebetween into which a selected generally flat portion of the retractor can be disposed; and
    a connection between the spaced-apart members along one edge thereof.

12. The apparatus of claim 5, wherein the locking mechanism comprises:
    a threaded opening in the clamp; and
    a threaded pin that extends through the threaded opening in the clamp, the threaded pin adapted to engage the selected generally flat portion of the retractor.

13. The apparatus of claim 5, wherein the clamp is connected to a generally flat portion included as part of either the first arm or the second arm.

* * * * *